United States Patent [19]

Stossel

[11] 3,945,987

[45] Mar. 23, 1976

[54] CARBAMIDE ADDUCTS OF POLYMETALOPHOSPHAMATE

[76] Inventor: Ernest Stossel, 203 W. 81st St., New York, N.Y. 10024

[22] Filed: May 30, 1974

[21] Appl. No.: 474,821

[52] U.S. Cl..... 260/96.5 C; 260/96.5 R; 260/555 R
[51] Int. Cl.² .......................................... C07B 21/00
[58] Field of Search ....... 260/96.5 R, 96.5 C, 555 R

[56] References Cited
UNITED STATES PATENTS

| | | | |
|---|---|---|---|
| 2,418,525 | 4/1947 | Pollak | 260/555 |
| 2,423,556 | 7/1947 | Feibelmann | 260/96.5 |
| 2,480,814 | 8/1949 | Punshon et al. | 260/555 |
| 3,297,425 | 1/1967 | Barbaras et al. | 260/96.5 |

Primary Examiner—Delbert E. Gantz
Assistant Examiner—C. E. Spresser
Attorney, Agent, or Firm—Michael J. Striker

[57] ABSTRACT

There is disclosed a method of forming a urea adduct complex by reacting an aluminum hydrogen phosphate complex which is normally unstable in solution at a pH greater than 2.5 with sufficient urea that no precipitation of alumina occurs on addition of ammonia, and adjusting the pH of the resultant urea adduct complex with ammonia to a value of from 2.5 to 10. The urea adduct complexes of the invention are fire retardants and fire quenching agents and are useful as agricultural adjuvants.

16 Claims, No Drawings

CARBAMIDE ADDUCTS OF POLYMETALOPHOSPHAMATE

This invention relates to new adducts of complex aluminum acid phosphates with urea and a neutralizing agent in particular proportions, which adducts are water soluble and convertible upon heating to a foamed flame resistant product, and to methods for making the same.

Complex aluminum acid phosphates are well known materials formed by reacting a concentrated solution of an acidic phosphate salt of aluminum and/or chromium in the presence of an excess of phosphoric acid with a compound having at least one $-NHR_2$ group, the hydrogen atom attached to the nitrogen in this group being labile. These compounds can be dissolved in water to form a highly acidic solution but attempts to neutralize such solutions result in precipitates when the pH thereof is raised above about 2.6. A detailed summary of the earlier literature relating to aluminum amidopolyphosphates is found in U.S. Pat. Nos. 3,414,374 and 3,667,903, the disclosures of which are incorporated hereby by reference.

U.S. Pat. No. 3,414,374 in particular discloses neutral water soluble ionic complexes containing phosphorus, oxygen, nitrogen, and aluminum and/or chromium in an anionic portion of the molecule which are soluble in or compatible with aqueous media having a pH above 2.5. The complexes are prepared by a process including a critical step of heating to a temperature above 180°C which is required to convert the unstable aluminum acid phosphate with its cationic form of aluminum to the stable complexes containing the aluminum in the anion. The materials used to prepare the anionic complexes are aluminum acid phosphate and a compound having at least one $-NHR_2$ group wherein $R_2$ is hydrogen or an organic or phosphoro-oxygen radical as defined in the patent. Certain $-NHR_2$ compounds including urea are defined as foaming $-NHR_2$ compounds. When these are used to prepare the complexes of the patent, foam is formed during the preparation. There is, however, no disclosure of any combination of aluminum acid phosphate, urea, and ammonia or other neutralizing agent that does not have the metal in the anion and which is stable at a pH above 2.6 and is capable of foaming upon being heated.

U.S. Pat. No. 3,667,903 discloses a process of preparing the anionic metal complexes of the earlier patent by a foam reaction technique under controlled conditions. The foaming reaction is applied to solutions of aluminum acid phosphate and urea with added phosphoric acid and water. Such solutions are highly acidic. There is no disclosure of any composition of aluminum acid phosphate, urea, and a neutralizing agent that is stable in aqueous solutions at a pH above 2.6 and can be subsequently foamed.

It is known that aluminum hydroxide dissolved in highly concentrated phosphoric acid yields aggregation polymer, resin-like compounds, in which the $PO_4$ is held together by aluminum ions in the form of a three dimensional molecular complex or network; the stability and degree of polymerization is, however, largely dependent upon the pH. The degree of polymerization of such polymers may range from 2 to 20,000 according to concentration, pH and temperature. Such aggregation polymers have the tentative formula $[NH_4H.Al(PO_3NH_2.H_2O)_4]_y$ and will be interchangeably referred to hereinafter as acid aluminum phosphates and aluminum amidopolyphosphate complexes and are considered similar to heteropoly acids and may represent a transition between heteropoly acids and metallosphosphoric acid complexes. These highly acid polyphosphate solutions have found many uses as binders in the manufacture of various products such as ceramics and adhesives. From their concentrated solutions, a rather tough film can be deposited on the surface of the substrate which renders flammable materials, e.g., cellulose, wood, etc. flameproof. However, the solutions or the resulting dry film are not compatible with acid sensitive pigments or alkaline compounds, since these aggregation polymer solutions are stable only at very low pHs, below 2.6; when the pH is brought above 2.6, the complex decomposes or precipitates.

It is, therefore, apparent that an acid aluminum phosphate that could be useful in the ways suggested by the prior art and also be stable in aqueous solution having a pH above 2.6 would fill a long standing need.

It has now been found that concentrated solutions of acid aluminum phosphate can be neutralized with ammonia without precipitation when the viscous acid aluminum phosphate solution in water is mixed with substantially solid urea at a temperature not exceeding about 90°C, to form a "clathrate". Thereafter addition and/or formation of ammonia by heating the adduct, the decomposition of urea takes place only at higher temperatures, increases the solubility of the acid ammonium phosphate in water; it seems that addition of urea causes a urea adduct to be formed in the solution which results in an increase in solubility, as has been found in many similar cases. Urea adduct complexes are widely used in many separation processes, for instance, in the petroleum industry for separation of straight chain paraffins from branched chain hydrocarbons.

It is known that urea forms complexes with many acids and salts; this complex building is not based, however, on a chemical reaction of the compound with urea, but on enclosure by the host molecule, i.e. urea, of the acid aluminum phosphate molecule which by its structure adapts itself to be enclosed within the urea molecule which then becomes a kind of "packaging" or cage. These complexes have, therefore, also given the name clathrate (from the latin name of clathri-bird-cages). This term will be used in the following description alternately with urea adduct complexes and urea inclusion complexes. The formation of urea clathrates takes place in most cases almost immediately when a concentrated solution of the acid aluminum phosphate compound in an appropriate solvent is mixed with a concentrated solution of urea. The urea can be subsequently decomposed by heat to form the stable neutralized water soluble adduct. These complexes are also formed in solution which is mostly indicated by an increase in solubility of the acid aluminum phosphate when the urea is added to the solution.

The above-described adduct of acid aluminum phosphate is easily and economically produced by the method of the present invention wherein an aluminum phosphate solution in aqueous phosphoric acid is concentrated until a semi-plastic, highly viscous solution is obtained which contains between 10 to 12% water. It has been found that the content of the resulting aluminum phosphate is highly enriched in metal-phosphoric compounds at such higher concentration. This highly viscous fluid is then cooled to below 90°C and in a second step, intimately mixed with solid urea to form a urea adduct complex. The semiplastic mass comprising the essential polymeric aluminum amidopolyphosphate complex becomes immediately fluid upon addition of urea. Urea is added until a sample does not undergo precipitation when treated with concentrated ammonia. The urea inclusion complex solution is very fluid and contains about 7% of water. Air drying for several days or drying, by heating for example at a temperature not exceeding 70°C reduces the solution to a powder which is soluble in about 10% of its weight in water. The fluid solution can be neutralized by ammonia gas to the required pH, in the well known and conventional manner to form a mixture of the clathrate and ammonium phosphates.

The urea dissolves rapidly in the viscous aluminum hydrogen phosphate solution causing it to form a thin liquid. In accordance with the invention at least about 2 moles of urea for about each 3 moles of acid aluminum phosphate are required for the formation of the adduct before further neutralization of ammonia can properly proceed. The neutralized urea adduct solutions set after several days to form a solid or can be dried and dehydrated to a powder at a temperature below about 80°C.

The buffered, acid solution of the above-described aluminum acid phosphate-urea clathrate and the neutralized admixture thereof with ammonium phosphates can be directly used for the impregnation of flammable materials as wood, paper, textiles, plastic foams, etc.

When the concentrated solution of the acid aluminum phosphate-urea clathrate is heated above a temperature of 150°C, a voluminous foam is formed which expands to up to about 100 fold its volume. When a temperature of 200°C is reached a hard cellular foam is formed which contains within its innumerable cells encapsulated carbon dioxide. Upon heating, the urea of the "host molecule" decomposes into carbon dioxide and ammonia, the latter reacting with the aluminum phosphate of the foam bubble skins, reinforcing and stabilizing the foam to such a degree that it resists bursting of the bubbles when the enclosed carbon dioxide increases in pressure, thus expanding the stabilized foam bubbles to extremely thin films and causing reactions, including dehydration to take place on the inner surface of the foam bubble films, almost at once. At 200°C, a complex is finally formed which contains nitrogen substituted for part of the molecular water of the phosphate molecule, and the metal in the anionic part of the newly formed ionic complex. This complex is neutral, readily water soluble and compatible with ammonia, alkaline pigments and emulsions. It is used for compounding water based paints, alone or in combination with known pigments for fire retardant coatings as guanyl phosphate, dipentaerithritol, phosphatized melamine formaldehyde, chlorowax, etc. and stable binders for intumescent ingredients.

As raw materials for use in this process, especially when the use of crude materials are permissible, for example for fire retardant compositions for upholstery or impregnation of plastic foams for building materials, a variety of ores can be worked up, e.g. bauxite, Wavellite (aluminum phosphate ore), kaolin, and aluminum phosphate ores (beneficiated leach zone, North African ores containing up to 30% $P_2O_5$ and 27% $Al_2O_3$ and a great variety of metal oxides of di- and trivalent materials, i.e. Zn, Fe, Mn, Mg, Cr, Ti and the impurities contained in the wet acid process phosphoric acid. The water solubility of the clathrates can be modified by reacting the urea complex with formaldehyde and its derivatives as is known in the art.

It has further been found that the concentrated clathrate solution when heated above a temperature of about 150°C, produces a voluminous foam which can be increased and stabilized when small percentages of heat resistant foaming agents are added to the solution before the heat treatment. Typically, there is employed the addition of surfactants from the series of fluorocarbons as disclosed in U.S. Pat. No. 3,667,903 such as the products available from MMM under the designations FC95 and FC98. They have been found to be effective in amounts of about 0.01% by weight, preferably about 0.01 to 0.1% for carrying out of the process called foam polymerization, in which the highly concentrated aluminum acid phosphate solution (about 80% solids), phosphoric acid, a blowing agent for instance urea and surface active agents are subjected to a temperature of about 150°C which blowing agent under the conditions of the reaction develops ammonia gas and carbon dioxide.

When the thermal reaction is performed under agitation, as by heating the clathrate solution containing the surfactant, between heated rollers or similar devices, a fine powder is obtained directly at about 200°C but when the foam reaction takes place without agitation, as e.g. by heating the concentrated solution in a heated chamber or in a microwave oven, a cellular inorganic blanket is formed which retains the pressurized carbon dioxide firmly within its cells; when the heating is the result of flame exposure of a substrate impregnated with the "solution" an inorganic cellular blanket is formed directly on the impregnated substrate and within the cells or pores protecting the flammable substrate from further contact with air or oxygen, quenching any flame or fire by the intumescent, inorganic blanket which contains within its cells the encapsulated, pressurized carbon dioxide. It increases its efficiency when the temperature or activity of the flame increases and the intumescence of the cellular blanket becomes more pronounced.

Broadly speaking, the invention includes the provision of adducts of an aluminum amidophosphate complex with urea, the complex having been formed by reacting a concentrated solution of an acidic phosphate salt of aluminum preferably in the presence of an excess of phosphoric acid with a compound having at least one $—NHR_2$ group wherein $R_2$ is hydrogen or an organic or phosphoro-oxygen radical.

The aluminum amidophosphate complex is adducted by the addition of about 2 moles of urea for each 3 moles of combined phosphoric acid prior to the neutralization thereof with ammonia. The addition of the urea is believed to result in the formation of a urea inclusion complex which serves as buffer for the acid solution and enables the neutralization step with ammonia to proceed without precipitation. The urea inclusion complex or adduct compound remains stable even when boiled in water. Upon heating to about 150°C, the urea of the "host molecule" is decomposed into carbon dioxide and ammonia which thereby causes the compound to foam. The volume and stabilization of the foam can, if desired, be greatly increased by the addition of small amounts of heat resistant foam surfactants thereto, preferably those of the fluoro-carbon group. Several reactions are believed to take place in foam phase; dehydration, expansion of the bubble skins, which are essentially composed of insoluble inorganic reaction products of the metal phosphates and ammonia developed by the decomposition of the urea. Eventually a complex is formed at about 200°C, when $NH_2$ groups are substituted for the molecular water of the phosphate. An ionic polymer is formed as a fine powder, which is neutral, water soluble and contains the metal as part of the anion. The water solutions are compatible with ammonia, alkaline pigments and emulsions.

The foams may be produced by thermal treatment known in the art, such as by heating the complex prepolymer solution on hot rollers, etc. or by passing it through a microwave oven hot chamber or the like.

It has been found, that the solution is an excellent impregnating agent for flammable substances, which, upon being treated to high temperatures or exposed to a flame or fire, are rendered flame-retardant and fire quenching. When heated, these substances become protected by the formation of a heat formed inorganic cellular blanket, which retains within its cells encapsulated pressurized carbon dioxide. This fire retardant or flame retardant has applications in the impregnation of porous materials and plastic foam products.

As stated above, the amount of urea required is preferably at least about 2 moles for about each 3 moles of combined phosphate acid. The amount of urea, however, can be as much as about 4 to 6 moles per mole of acid phosphate. Larger amounts contribute little additional advantage and are generally uneconomical. The amount of neutralizing agent will generally be based on the quantity necessary to adjust the pH to the desired value, typically about 1 to 20 moles per mole of phosphate. The final pH of the solution of the adducts of this invention will be higher than about 2.6 and can range as high as about 10, a preferred range being about 3.5 to 8.

The preferred neutralizing agent is ammonia which can be supplied in the form of ammonia gas or an aqueous solution thereof. Additional neutralizing agents that can be used include ammonium carbonate, ammonium carbamate, ammonium bicarbonate, ammonium borate, ammonium sesquicarbonate, and the like as well as the ammonium salts of organic acids such as ammonium acetate, ammonium benzoate and the like. A general formula for the neutralizing agent is $NH_4X$ wherein X is an anion of the kind specified above.

The adducts of the invention are believed to correspond to the general formula

wherein $a$ is an integer of about 2 to 9, $b$ is an integer of about 1 to about 20 and $c$ is an integer of about 1 to 20.

The process of preparing the aluminum amidophosphate has been described in detail in U.S. Pat. No. 3,414,374.

The method of preparing the foams has been described in U.S. Pat. No. 3,667,903.

The following Examples which are not intended to limit the invention in any way are submitted only for the purpose of illustration without limiting the invention to the specific details thereof. The invention might be performed in a wide variety of ways. All parts, proportions and percentages, employed herein, as well as in the appended claims are by weight unless otherwise indicated.

EXAMPLE 1

160 g Of aluminum hydroxide was dissolved in small increments, with stirring, in 1080 g of 75% aqueous orthophosphoric acid. The heat liberated during the reaction was sufficient to bring the temperature of the reaction mixture almost to the boiling point. The heat necessary to bring the reaction mixture to boiling was supplied, and boiling and stirring continued with removal of water until the temperature was brought to 125°C. To the hot solution containing aluminum hydroxide and phosphoric acid in the molar ratio of 1:4, was added 480 g of urea and then heated to form a liquid which contains about 80% solids to about 125; the solution becomes very viscous. The temperature is then reduced to below 90°C and is hardly fluid. When a small quantity of aqueous ammonia is added to a sample of this liquid, an immediate precipitate forms until no further stirring is possible. Addition of a small amount of urea to another sample results in a liquifying of the material. The amount of urea necessary for forming an adduct can simply be determined by gradually adding urea until a sample treated with urea does not show precipitation upon addition of ammonia.

In this Example, to the indicated amount of concentrated acid aluminum phosphate solution, there is added 200 grams of urea powder which dissolves immediately in the viscous solution liquifying it to a fluid. In this liquid there is dissolved about 0.01% of a foaming heat resistant fluorocarbon surfactant (3M, FC 95 or 98 or ICI Atlas Monoflor) and the liquid is subsequently dried at low temperature (air dried or force dried below 70°C) to powder. This compound will hereinafter be called Compound A and is soluble to about 20% of its weight in water and reacts as an acid. Due to its high content of urea adduct complex, it is highly buffered and can be applied to substrates which are not too sensitive to acids. When Compound A or its concentrated solution is applied for the impregnation of materials to render them fire resistant, the impregnation serves as an intumescent protection in case of fire as will be described in Example 4.

EXAMPLE 2

The urea adduct complex solution as described in Example 1 containing aluminum phosphate, aqueous phosphoric acid, urea and foaming agent surfactant in a proportion of 1 mole $Al(H_2PO_4)_3$, 1 mole $H_3PO_4$, 4 moles urea, 7 moles $H_2O$ is poured evenly onto the top of the drums of a double-drum dryer, heated by oil or direct firing to a drum surface temperature of 220°C. The heating of the drums is adjusted to compensate for heat losses due to evaporation of water so that a constant surface temperature of 200°C can be maintained. The drum clearance is 0.8 so that at the process temperature, no liquid can pass between the drums, and the drum speed adjusted so that the drums are always covered with the heavy foam formed between the drums. When the liquid contacts the heated drums, it is carried away in hardened form through the clearning between the drums and scraped off by means of conventional knives. The whole reaction takes place under evaporation of water, decomposition of the host molecule, into carbon dioxide and ammonia, reaction of ammonia with the dehydrated solution of aluminum phosphate and eventually, substitution of the molecular water of the phosphate molecule by nitrogen and polymerization to an ionic complex of an aluminum amidophosphate which had earlier been characterized by the formula $NH_4H-[Al(PO_3NH_2H_2O)_3]_n$ wherein the metal forms part of the anion. The polymer is soluble in water and ammonia and shows no reactions of cationic aluminum, is compatible with alkaline compounds, pigments and emulsions used in paint manufacturing as binders. In this Example the adduct has been converted into the complex with highly favorable properties.

EXAMPLE 3

The Compound A prepared according to Example 2 is intimately mixed with half its weight of powdered urea at a temperature below 70°C. The mixture is heated for 1 hour at 95°–100°C to provide ammonia by the thermal decomposition of the urea to carbon dioxide and ammonia. Upon dissolving this mixture in 30% of water, a fluid urea inclusion complex is formed which is used as a flame retardant impregnation, or can be dried to a crystalline compound of well defined long needles which are easily soluble in water.

A dry mixture of 55% of the above urea adduct, 27% urea together and 18% sorbitol is prepared. This powdered mixture is dissolved in 30 parts water to 100 parts of adduct to form a very fluid solution. Porous flammable materials, paper, polyurethane sponge, wood, and the like are impregnated with this fluid solution which due to its low viscosity penetrates into the pores of the substrate, easily, but thickens within the pores and sets eventually to form a stiff gel. When the impregnated substrate is excessively heated by flame or fire, the clathrate gel impregnation forms an intumescent coating protecting the substrate from contact with air and quenching the fire, immediately. The performance of the compound with regard to modification of solubility in water and resistance to moisture, can be improved in the conventional manner, by for instance, adding formaldehyde to the solution water.

EXAMPLE 4

An aluminum phosphate urea adduct solution prepared according to Example 1, neutralized with ammonia is used for impregnating polyurethane sponges, and the sponges dried. The clathrate solution is plasticized by the addition of 15% liquid chlorinated paraffin. Upon exposing the impregnated sponges to a flame, the impregnation forms a solid, inorganic foam blanket with the encapsulating pressurized carbon dioxide inhibiting the propagation of fire.

EXAMPLE 5

100 Grams of bauxite (58% $Al_2O_3$, 1.2% $Fe_2O_3$, 6% $SiO_2$, 2.2% $TiO_2$) are added to 800 g 50% orthophosphoric acid and the mixture brought to the boiling point. The solution is separated from undissolved residue. The clear solution is heated to a temperature of 125°C and then thereafter cooled to 90°C, as in Example 1, then mixed with 250 g of powdered urea, 20 g of boric acid and 20 g of zinc-oxide and also 0.1% of fluorocarbon foaming agent and worked up according to Example 1 or Example 3.

EXAMPLE 6

Aluminum phosphate ore analysis: $Al_2O_3$ 31%; $P_2O_5$ 22.5%; Ca 0.9%; $Fe_2O_3$ 7%; $SiO_2$ 2.5%; $TiO_2$ 1.5%; water 16%) 100 parts of this aluminum phosphate ore are heated and digested with 250 parts of phosphoric acid and 55 parts of 98% sulfuric acid for 1 hour at 100°C, the supernatant liquid separated after cooling to 50°C from any undissolved residues. The clear liquid is then heated to 125°C and evaporated to a semi-plastic viscous mass. After cooling to 80°C 200 grams of powdered urea are mixed into the liquid which becomes free flowing and finally very fluid and fairly transparent. This liquid can be added directly to other materials for forming fire fighting foams. The clathrate solution is converted by fire or flames to a lightweight cellular blanket which retains pressurized carbon dioxide encapsulated in its cells and floats to the surface of burning liquids (oil fires) extinguishing the fire immediately.

EXAMPLE 7

The aluminum phosphate urea inclusion solution prepared according to Examples 4 and 6 is placed on a metal band in a microwave oven where it blows immediately to form a heavy foam and is converted as in Example 2 to the nitrogen-containing polymer of nearly neutral reaction (pH 6–7) which shows the metal as part of the anion as in Example 2.

EXAMPLE 8

An adduct composition is prepared from 70 parts of polymer according to Examples 1, 2, 4 and 6, and 30 parts of urea in 45 parts of water. A uniform dispersion is formed which slowly thickens without separation of solids even on prolonged standing. The thickened solution can be diluted with water and applied most advantageously as a fertilizer. It is also possible to recover the adduct in dry form. In powder form it contains phosphorus pentoxide - 39.9%, nitrogen - 23.2% and aluminum oxide - 7%. It is slightly hygroscopic.

EXAMPLE 9

A composition is prepared according to Example 1, whereby a water soluble complex of the formula $NH_4H[Al(PO_3NH_2H_2O)_{3-4}]_n$ is obtained 100 grams of this aluminum amidophosphate polymer is mixed with 50 grams of urea. This composition when dissolved in 30 to 50 parts of water forms upon standing for several hours a urea adduct of the polymer. A fluid solution is first formed, then a colloidal solution, a jelly and eventually a stiff gel. Depending on the amount of water to the amount of adduct the solution can be applied as a thin liquid to impregnate porous materials for improving their fire retardant properties.

EXAMPLE 10

In order to prepare a compound with high nitrogen content and high content of phosphoroxide which can be applied as fertilizer a compound was prepared mixing 100 grams of polyamidophosphate and 100 grams of urea, and dissolving the mixture in 2 and ½ parts of water. The colloidal solution penetrates into the soil where the colloidal particles adhere to the earth due to the highly adhesive characteristics of the solution.

EXAMPLE 11

A solution as described in Example 10 was prepared and diluted with water as needed. This solution can be used as flame retardant, adhesive for plywood, paper panels, paper coating, etc.

Without further analysis, the foregoing will so fully reveal the gist of the present invention that others can by applying current knowledge readily adapt it for various applications without omitting features that, from the standpoint of prior art fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. An alkali stable water soluble adduct of an aluminum amido polyphosphate complex having the formula [NH$_4$H Al(PO$_3$NH$_2$.H$_2$O)$_4$]$_y$ with urea.

2. An adduct according to claim 1 wherein 2-6 moles of urea are present for every 3 moles of bound phosphoric acid.

3. An adduct according to claim 1 wherein at least 2 moles of urea are present for every 3 moles of bound phosphoric acid.

4. An adduct according to claim 1 having the following formula

wherein $a$ is an integer of about 2 to 9, $b$ is an integer of about 1 to 20 and $c$ is an integer of about 1 to 20 and X is a substance selected from the group consisting of "carbonate, carbamate, bicarbonate, borate, sesquicarbonate, acetate and benzoate."

5. A method of preparing the adduct of claim 1 which comprises adding urea to a solution of an aluminum amidophosphate complex, wherein said urea is used in an amount of at least 2 moles for every 3 moles of phosphoric acid present in said phosphate.

6. Method according to claim 5 wherein said urea is used in an amount of at least 2, up to 6 moles per mole of phosphoric acid present in said phosphate.

7. Method according to claim 5 which comprises adjusting the pH of the resultant urea adduct complex with ammonia or an ammonia producing compound to a value of from 2.5 to 10.

8. Method according to claim 7 which comprises adjusting the pH to a value of 3.5 to 8.0.

9. Method according to claim 7 wherein ammonia is used in the form of a gas.

10. Method according to claim 5 wherein the water content of said phosphate complex does not exceed about 10%.

11. Method according to claim 7 which comprises adjusting the pH of the urea adduct complex by heating the same to a temperature above 150°C wherein a part of the urea present in said adduct is decomposed to ammonia and CO$_2$ and said ammonia serves to neutralize said urea adduct.

12. Method according to claim 11 wherein said heating is carried out in the presence of a fluorocarbon surfactant foaming agent and a foam is thereby formed.

13. Method according to claim 12 wherein said surfactant is used in an amount of about 0.01 to 0.1%.

14. A flame proofing composition comprising an adduct complex according to claim 1.

15. A fertilizer composition comprising an adduct complex according to claim 1.

16. A composition comprising a mixture of polymetalophosphamate prepared by heating acid metalohydrogen phosphate and urea to from 180°–200°C to form amidopolyphosphate complex according to claim 1 with additional urea to compensate for the urea used up by the thermal decomposition during the preparation of the amidopolyphosphate complex so as to obtain an easily soluble compound containing from 10 to 40% of nitrogen and eventually dissolving the mixture for use with 30 to 50% of water to obtain a colloidal solution.

* * * * *